United States Patent [19]
Daniell

[11] Patent Number: 4,976,718
[45] Date of Patent: Dec. 11, 1990

[54] PARASITE REMOVER

[76] Inventor: Christopher H. Daniell, R.R. 4, P.O. Box 186, Hopkinton, N.H. 03229

[21] Appl. No.: 369,305

[22] Filed: Jun. 21, 1989

[51] Int. Cl.$^5$ .............................................. A61B 17/50
[52] U.S. Cl. .................................... 606/131; 606/210; 294/99.2; 294/902; D24/27
[58] Field of Search ................................. 606/205–207, 606/210, 211, 131, 138; 294/99.2, 902; D24/27; D28/55

[56] References Cited

U.S. PATENT DOCUMENTS

| | | | |
|---|---|---|---|
| D. 190,357 | 5/1961 | Crow | D24/27 |
| 223,066 | 12/1879 | Russell, Jr. | 294/99.2 X |
| 523,300 | 8/1894 | Whisson | |
| 1,141,741 | 6/1915 | Wiseman | 294/99.2 X |
| 1,461,670 | 7/1923 | Mills | 294/99.2 X |
| 2,376,448 | 5/1945 | Neugass | |
| 2,644,455 | 7/1953 | Benoit | |
| 4,213,460 | 7/1980 | Weiner | 606/205 X |
| 4,303,268 | 12/1981 | Davidson | 606/210 X |
| 4,442,837 | 4/1984 | Keatley | |
| 4,728,139 | 3/1988 | Oretti | 294/99.2 |

FOREIGN PATENT DOCUMENTS 2483770 12/1981 France .

OTHER PUBLICATIONS

"Evaluation of Five Popular Methods for Tick Removal", by G. R. Needham, *Pediatrics*, vol. 75, No. 6, Jun. 1985.
"Watch Out for the Tick Attack", *Consumer Reports*, Jun. 1988.
"Composition of Tick Oral Secretions Obtained by Three Different Collection Methods", by R. W. Barker et al., *Journal of Medical Entomology*, vol. 10, No. 2, Apr. 1973.
"Chapter VI—Capitulum and Feeding Mechanism", *Ticks and Disease*.
"Tick-Borne Dermatologic Diseases", C. E. Modly and J. W. Burnett, *Environment Versus Man*, vol. 41, Apr. 1988.
"Duration of Tick Attachment and Borrelia Burgdorferi Transmission", by Peisman et al., *Journal of Clinical Microbiology*, Mar. 1987.
"Tick-Kit Instructions", manufactured by Tick-Kit Incorporated, P.O. Box 2082, Amagansett, N.Y.

*Primary Examiner*—Mickey Yu
*Attorney, Agent, or Firm*—Wolf, Greenfield & Sacks

[57] ABSTRACT

A forceps for removing a parasite such as a tick from a human or animal host where the parasite has attached itself to the host at its head and the parasite contains fluids which can be expelled into the host upon the application of an external squeezing force, particularly a squeezing force applied to the body of the parasite. The forceps includes first and second arms each having a distal end and a proximal end and secured so that they are movable in opposition to one another between an open position and a closed position. A gripping section for engaging the parasite is mounted on the distal end of the forceps. The gripping section includes first and second sets of interdigitating teeth mounted on each of the opposed arms that are sized to closely surround the body of the parasite without crushing or squeezing any part of the parasite's body when the arms are in the closed position. The gripping section also has a portion mounted at the extreme distal end of the opposed arms with an oval opening formed in the extreme end portion when the opposed arms are in their closed position. The oval opening acts to closely grip and surround the head or neck of the parasite without crushing it. The parasite can be completely and quickly removed from the host without causing the parasite to expel disease containing fluids back into the host.

22 Claims, 2 Drawing Sheets

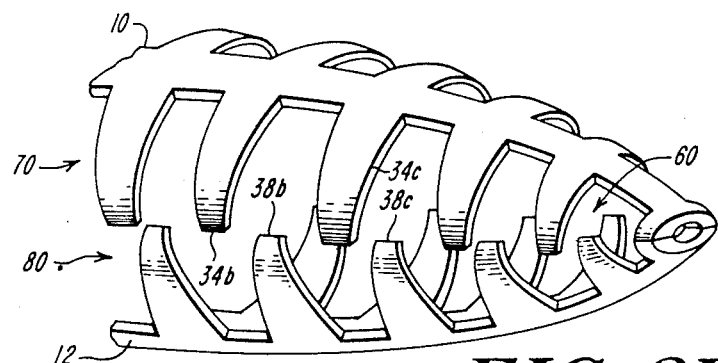
*FIG. 3B*
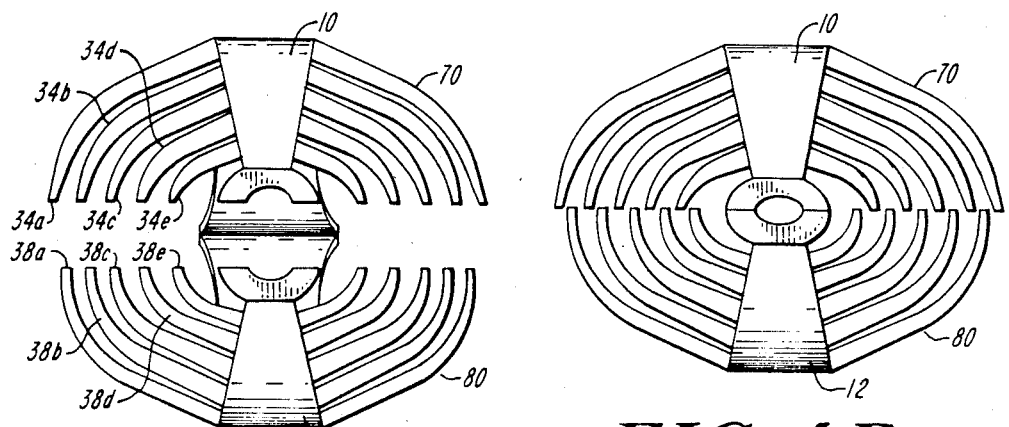
*FIG. 4A*  *FIG. 4B*
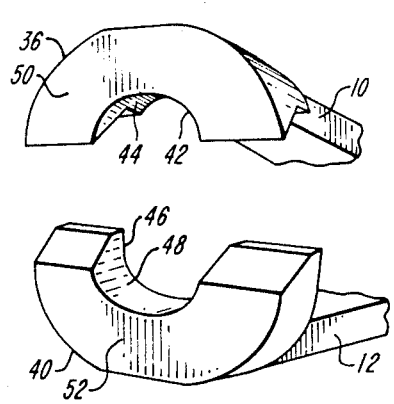  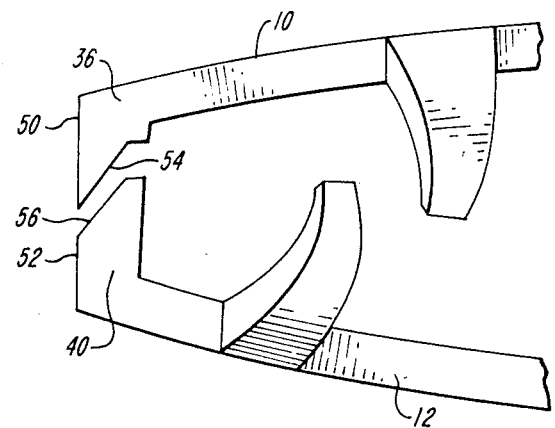
*FIG. 5*  *FIG. 6*

PARASITE REMOVER

BACKGROUND OF THE INVENTION

1. Field of the Invention

The present invention relates generally to the field of surgical instruments and more particularly, to the field of forceps or tweezers for removing a parasite such as a tick from a host animal.

2. Description of the Prior Art

In recent years, there has been an alarming increase in the incidence and geographical range of tick-born disease. Both humans and animals are affected by a number of infectious agents carried in and transmitted by ticks, such as Rocky Mountain Spotted Fever and Lyme disease.

When a tick attaches to a host which may be a human or an animal, it not only inserts a portion of its mouthparts into the host to reach the blood supply, it also secretes an adherent cement onto the skin of the host which helps prevent the tick from becoming detached from the host. After the tick attaches to the host, infectious agents within the tick may be transmitted to the host by the tick during its feeding cycle. However, several hours may elapse after attachment before infectious agents are transmitted and consequently, the sooner the tick is removed, the lower the risk of infectious agents being transmitted to the host. Therefore, the best method of protecting the host from any diseases carried by the tick is a rapid, effective, and complete removal of the tick from the host.

One prior art method for removing ticks from the host is through the use of chemical agents such as petroleum jelly, fingernail polish and alcohol. In theory, the chemical agent should either kill the tick or cause the tick to release itself from the host. However, in practice, chemical agents have simply not proven to be effective. See, for example, Glen R. Needham, in "Evaluation of Five Popular Methods for Tick Removal", *PEDIATRICS*, Vol. 75, No. 6 (June, 1985). First, they simply do not cause the tick to remove itself from the host reliably, nor do they quickly kill the tick. In fact, a potential problem with chemical agents is that the chemical agent may irritate the tick and thereby stimulate it to transmit infectious agents to the host. Another problem is that chemical agents which do stimulate the tick to detach from the host will not also reliably remove the adherent cement excreted by the tick. It usually remains on the skin of the host after the tick detaches. The adherent cement may carry infectious agents itself or it may leave a wound in the skin of the host. In either case, the risk of infection is increased. Of course, another major drawback of chemical agents is that they must be available for use within hours after the tick attaches. It is often not possible to bring a person or animal to a supply of the chemical agent quickly enough. Alternatively, it is unlikely that people involved in outdoor recreation will carry a supply of a tick removal agent with them at all times.

Therefore, ideally, the best method to prevent transmission of disease from the tick to the host is complete removal of the tick and the adherent cement by mechanical means. However, a problem inherent in mechanical systems is that care must be exercised to avoid squeezing or crushing the body of the tick during removal because saliva, hemolymph, or gut contents which contain infectious agents can be regurgitated into the human or animal host.

Another important consideration when mechanically removing the tick from the host is to prevent accidental contact with infected tick body fluids. Infectious agents can enter a break in the skin of either the host or the person removing the tick. Consequently, direct contact with the tick should be avoided.

In order to effect mechanical removal of the tick from the host, a number of prior art forceps or tweezers have been developed. One problem with forceps of the prior art is that they rely on pressure against the body of the tick in order to obtain an adequate purchase for removal. In other words, they clamp the body of the tick like a pair of pliers. Any squeezing of the body of the tick may cause the infected bodily fluids of the tick to be expelled to the host. Another problem with the prior art tick removal forceps is that the tips are designed to clamp solidly together in continuous full surface contact. This makes removal of ticks in hair bearing areas or in folds or creases of the host's skin difficult because the host's skin may be pinched or the host's hair may be pulled. Discomfort to the host makes removal of the tick more traumatic, particularly if the host is a child or an animal.

An example of the prior art tick removing forceps is taught in U.S. Pat. No. 4,213,460. The forceps has a large handle that is attached to two closeable arms with a spoon-like structure mounted on the end of each arm. When the two arms are squeezed together, the spoon-like structure encloses and surrounds the tick. The large handle contains either a battery for supplying current to a heating element located in the spoon-like structure, or a supply of a chemical agent that would be released into the spoon-like structure in order to cause the tick to release its bite. Release of the tick depends on application of a noxious or irritating stimulus to induce withdrawal. As noted earlier, in practice, the use of chemical agents has not proven effective. Furthermore, as noted in the aforementioned Needham article "Evaluation of Five Popular Methods for Tick Removal", applying heat to a tick proved ineffective in inducing the tick to withdraw. A final disadvantage of this tick removal forceps is that it is large, bulky, and would be expensive to manufacture.

Another example of the prior art tick removal apparatus is taught in French Patent No. 2,483,770. The tip of this instrument has a ribbed surface on each of the two inner faces for pressing against and gripping the body of the tick in order to obtain an adequate purchase for removal. This instrument has several disadvantages. First, it actually squeezes the body of the tick in order to grasp it, which may cause the body of the tick to break thus releasing infectious fluids onto the skin of the host. Second, squeezing the tick may only pump fluids from the tick directly into the host through the feeding wound.

A final example of the prior art tick removal apparatus is taught in U.S. Pat. No. 4,442,837. This device has two closeable arms which can be locked in their closed position to grip the tick. This device suffers from the disadvantages of other prior art apparatus in that it relies on tight, physical grasping of the body of the tick in order to be able to remove it.

It is therefore an object of the present invention to provide a parasite removal forceps capable of grasping engorged and unengorged parasites, such as ticks, to effect their removal from the host without causing the parasite to expel infected fluids into the host.

Another object of the present invention is to provide a parasite removal forceps that atraumatically encases the parasite to allow additional purchase during removal from the host.

Another object of the present invention is to provide a simple, inexpensive, and effective apparatus for removing parasites from a host while affording maximum protection from disease to both the host and the person removing the parasite.

Another object of the present invention is to provide a forceps for removing parasites that is easy to use, even by one not skilled in the medical arts.

Another object of the present invention is to provide forceps for removing parsites that can accomodate a variety of types of parsites and a variety of sizes of each type of parasite.

Another object of the present invention is to provide a forceps for removing parasites that can be manufactured out of sterilizable materials, such as stainless steel or metal alloy.

Yet another object of the present invention is to provide a forceps for removing parasites that can be manufactured at low cost including molding the forceps from a plastic material.

SUMMARY OF THE INVENTION

The foregoing and other objects and advantages of the present invention are achieved in a forceps which has first and second opposed arms each arm having a distal end and a proximal end. The opposed arms are secured so that they are movable in opposition to one another between an open position and a closed position. A gripping section according to the present invention is mounted on the distal end of the opposed arms. The gripping section is formed to engage or capture the parasite by gripping the parasite without causing expulsion of any fluids from the parasite into the host when the opposed arms are in the closed position.

In a preferred form, the gripping section comprises first and second sets of concave enveloping "teeth" mounted on the distal end of the opposed arms, respectively. The two sets of concave teeth interdigitate when the opposed arms are in their closed position. The first and second sets of concave teeth are configured and sized to substantially enclose the body of the parasite when the forceps is in the closed position.

The gripping section of the forceps further includes a distal tip at the extreme distal end of the forceps. The distal tip comprises two end portions that project transversely from each of the opposed arms. An opening is formed in the end portions that is sized to closely surround the head or neck of the parasite when the arms are in the closed position.

In a preferred embodiment of the present invention, the opening in the end portions is of an oval shape. One surface of one of the end portions has an acutely angled surface that mates with a surface on the opposite end portion when the opposed arms are in the closed position.

The forceps, the interdigitating teeth, and the opening in the distal end are sized in order to accommodate the parasite to be removed. The forceps of the present invention may be made out of a number of materials, such as stainless steel, metal alloy or plastic.

The foregoing and other objects, features, and advantages of the present invention will be more readily understood and apparent from the following detailed description of the invention, which should be read in conjunction with the accompanying drawings, and from the claims which are appended at the end of the detailed description.

BRIEF DESCRIPTION OF THE DRAWINGS

FIG. 3B is a view corresponding to FIG. 3A showing the gripping section in a closed position;

FIG. 4A is a view in side elevation of the forceps shown in FIGS. 1-3B in an open position;

FIG. 4B is a view corresponding to FIG. 4A with the forceps in a closed position;

FIG. 5 is a detailed perspective view of the distal tip of the forceps shown in FIGS. 1-4B; and FIG. 6 is a view in side elevation shown in FIG. 5 of the distal tip.

DESCRIPTION OF THE PREFERRED EMBODIMENT

Figure 1:
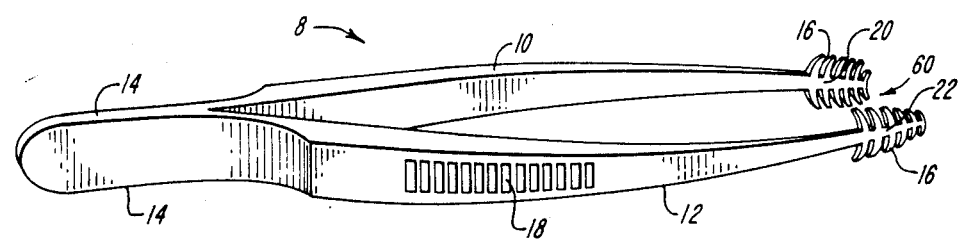
FIG. 1 is a perspective view of the forceps of the present invention.
Figure 2:
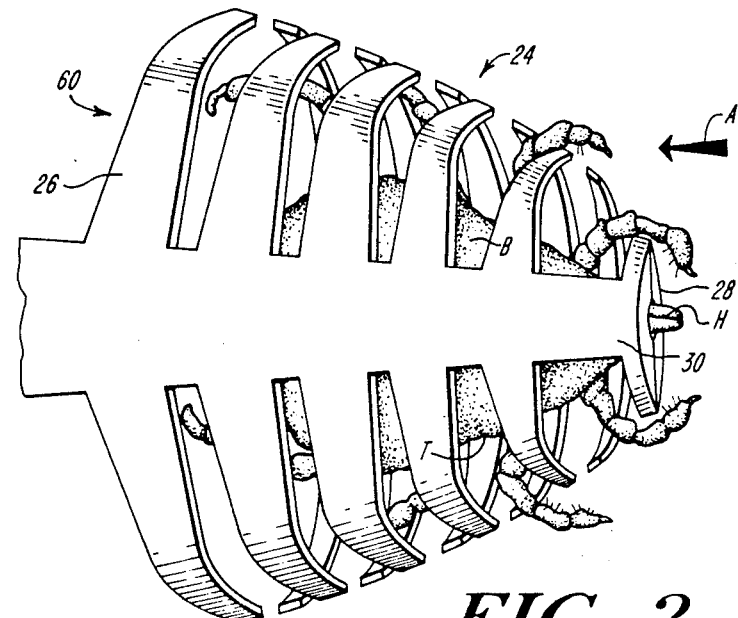
FIG. 2 is a detailed view, in perspective, of the gripping section of the forceps shown in FIG. 1, with the forceps in a closed position about a parasite such as a tick.

FIGS. 1-6 show of a forceps constructed according to the present invention and adapted for use in removing a parasite. For purposes of illustration only, and not to limit the scope of the present invention, the parasite will be considered to be a tick T which has a body B and a head H as shown in FIG. 2. The head of the tick is smaller is cross-sectional area than the body. The body of the tick may be engorged or unengorged depending upon the stage of the feeding cycle that the tick is in.

Referring to FIG. 1, the forceps 8 has two opposed arms, 10 and 12 which may be made of a variety of structural materials, such as stainless steel, metal alloy or plastic that are rigid and preferably sterilizable. Each of the opposed arms has a proximal end 14 and a distal end 16. The opposed arms are joined their proximal ends 14. The forceps 8 shown in FIG. 1 is shown in the open position. When in its open position, the arms 10 and 12 are spaced a sufficient distance to clear the body of a parasite. The opposing arms may be grooved on the outer surface at 18 in order to provide a non-slip grasping area for the person using the forceps. For use in removing larger size ticks, such as those that carry Rocky Mountain Spotted Fever, the forceps is approximately 14 centimeters in length. For use in removing smaller sized ticks, such as those that carry Lyme disease, the forceps is approximately 6 centimeters in length.

At the distal end of the forceps 8, there is provided a gripping section comprising gripping portions 20 and 22 for engaging the tick in a manner which allows the tick to be forcibly removed from a human or animal host to which it has attached itself, but without also causing an expulsion of fluids from the tick into the host. The gripping portions 20 and 22 are mounted at the distal ends of each of the opposed arms 10 and 12, respectively.

FIG. 2 shows an enlarged view of the gripping section 24 when the opposed arms are in a closed position engaging a tick. The gripping section 24 has two major parts. The first part includes two sets of mutually spaced concavely shaped enclosing teeth 26 which are mounted to and extend substantially transversely from the opposed arms 10 and 12. The second part of the gripping section 24 includes a distal tip 28 mounted at the extreme distal end 30 of the forceps 8. When a tick is gripped as shown in FIG. 2, removal of the tick is accomplished by simply pulling the forceps 8 away form the host in a direction A aligned generally with the longitudinal axis of the forceps while the forceps are maintained in the closed position, as shown. The cement collar is removed along with the tick.

Figure 3A:
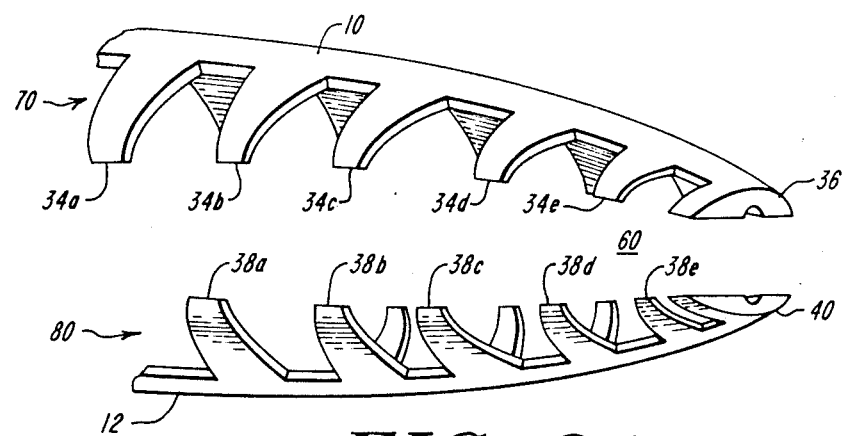
FIG. 3A is a perspective view of the gripping section shown in FIGS. 1 and 2 in an open position.

As shown in FIG. 3A and 4A, the gripping section 24 of the forceps 8 is designed and sized to clear the body of the tick when the opposed 10 and 12 are in the open position. Gripping portion 20 is composed of teeth set 70 and end portion 36. Teeth set 70 includes teeth 34a, 34b, 34c, 34d, and 34e. Gripping portion 22 is composed of teeth set 80 and end portion 40. Teeth set 80 includes teeth 38a, 38b, 38c, 38d, and 38e. Teeth 34a, 34b, 34c, 34d, and 34e extend transversely from opposed arm 10. Teeth 38a, 38b, 38c, 38d, and 38e extend transversely from opposed arm 12. When opposed arms 10 and 12 are brought to their closed position as shown in FIG. 3B, a concavity 60 is formed between rib set 70 and teeth set 80 which surrounds and contains the tick. It should be noted that when opposed arms 10 and 12 are brought to their closed position, the two opposing sets of teeth, teeth set 70 and teeth set 80 interdigtate as shown in FIGS. 3B and 4B. For example, in FIG. 3B, tooth 34c falls between teeth 38b and 38c while tooth 38b falls between teeth 34b and 34c.

Also, the individual teeth that makeup teeth set 70 and teeth set 80 also monotonically increase in size from the distal end 30 to the proximal end 14 of forceps 8 as shown in FIG. 2, 4A, and 4B. Tooth 34a is larger than tooth 34b which in turn is larger than tooth 34c which in turn larger than tooth 34d which is in turn larger than tooth 34e. Also, tooth 38a is larger than tooth 38b which is in turn larger than tooth 38c which is in turn larger than tooth 38d which is in turn larger than individual tooth 38e.

The design of the enclosing concavity 60 provides several important advantages. First, since the individual teeth are mutually spaced along the enclosed arms 10 and 12, and interdigitate, the body or legs of a tick captured or enclosed in concavity 60 will not be crushed or squeezed. However, the teeth can provide some additional purchase on the body or appendages of the tick to assist in its removal. Second, since the teeth increase in size monotonically from the distal end of the opposed arms to the proximal end, the concavity 60 is able to accommodate various sized ticks. In particular, the design of the concavity allows it to accommodate ticks in both the unengorged and engorged states. Third, since the teeth interdigitate and do not clamp tightly against each other, removal of tick in hair bearing areas of the host is facilitated.

The second part of the gripping section 24 is the distal tip 28. The distal tip 28 includes end portions 36 and 40 mounted to opposed arms 10 and 12, respectively. As shown in FIG. 5, end portion 36 is mounted transversely to opposed arm 10 and extends towards arm 12. End portion 40 is mounted transversely to opposed arm 12 and extends towards opposed arm 10. End portion 36 has, in its preferred form, a semi-oval opening 42 formed in surface 44. End portion 40 has a semi-oval opening 46 formed in surface 48.

As shown in FIG. 6, end portion 36 further includes a flat end surface 50 which is substantially perpendicular to opposed arm 10. End portion 40 further includes a flat end surface 52 which is substantially perpendicular to opposed arm 12. End portion 36 also has a surface 54 which is acutely angled with respect to flat end surface 50. End portion 40 has an angled surface 56 which meets with surface 54 when opposed arms 10 and 12 are brought to their closed position.

The design of distal tip 28 has several important advantages. First, when opposed arms 10 and 12 are brought to their closed positions, an oval opening is formed by the approximation of semi-oval openings 42 and 46. The oval opening thus created closely surrounds the head or neck of the tick without pinching or squeezing any part of the tick. Second, flat end surfaces 50 and 52 of end portions 36 and 40, respectively, allow the forceps to be placed directly against the skin of the host. Third, acutely angled surface 54 and its mating surface 56 provides a wedging action with respect to the shoulder or body of the tick as the forceps 8 and the gripped tick are pulled away from the host to remove the tick and the cement collar. The design of the distal tip 28 thus allows a solid purchase for removal to be gained on the tick without squeezing the head or the neck of the tick or causing the tick to expel fluids into the host.

The combination of the distal tip 28 and the interdigitating enclosing teeth sets 70 and 80, which together form the gripping section 24, provides a forceps which may be used to grasp ticks that are located in hair bearing areas of the host or that have securely attached themselves to the host. Further, the design does not irritate or squeeze any portion of the tick which would cause it to regurgitate or otherwise expel infectious fluids into the host. Finally, the design of the forceps of the present invention presents a low cost of manufacture. It is even possible to mold the forceps as a unitary structure, or in component parts, from a plastic.

Having thus described one particular embodiment of the invention, various alterations, modifications, and improvements will readily occur to those skilled in the art. For example, while the invention has been described with respect to its preferred embodiment which has interdigitating enveloping teeth, it is possible to construct a forceps which provides certain of the advantages of the present invention, but with the outwardly bowed portion of the forceps surrounding the tick body being solid, or substantially solid. This and other such alterations, modifications, and improvements as are made obvious by this disclosure are intended to be part of this description though not expressly stated herein, and are intended to be within the spirit and scope of the invention. Accordingly, the foregoing description is by way of example only and is not intended as limiting. The invention is limited only as defined in the following claims and the equivalents thereto.

What is claimed is:

1. Forceps for removing a parasite such as a tick from a host animal, said parasite having a body and a head smaller in cross-sectional area than the body, where the parasite has attached itself to the host at its head and the parasite contains fluids which can be expelled into the host animal upon the application of an external squeezing force, particularly a squeezing force applied to its body, comprising:

first and second opposed arms each having a distal end and a proximal end and each arm extending generally along a first direction;

means for securing said first and second arms so that they are movable in opposition to one another between an open position and a closed position in which said distal ends of said opposed arms are in contact with each other;

means mounted on said distal ends of said opposed arms for gripping the parasite, said means for gripping being formed to engage said parasite without applying a squeezing force to any part of the parasite and with a surface positioning to abut the body of the parasite when said arms are in said closed position, and spaced from one another a sufficient distance to clear the body of the parasite when said arms are in said open position;

whereby when said forceps are closed on a parasite that has attached itself to the host animal without the use of an irritating stimulus, a movement of the forceps in a direction away from the host animal causes said abutting surface to obtain purchase on the body of the parasite and removes the parasite without squeezing the parasite so as to expel fluids from the parasite into the host animal.

2. The forceps as claimed in claim 1 in which said means for gripping further comprises a concave structure that surrounds the body of said parasite without crushing any part of the parasite when said arms are in said closed position and an opening formed in said extreme distal end of said means for gripping and located at the extreme distal end of each of said arms, which is configured and sized to surround closely the head or neck of the parasite when said arms are in said closed position.

3. The forceps as claimed in claim 2 in which said means for gripping further comprises an end portion protecting substantially transversely to said first direction from each of said opposed arms and extending towards the other one of said opposed arms and said opening is formed in said end portion.

4. The forceps as claimed in claim 3 in which said concave structure comprises first and second teeth means, each of said first and second teeth means being curved to define a concavity and mounted to said opposed arms and extending generally transversely to said first direction;

said teeth means arrayed in a mutually spaced relation along said first direction 5. The forceps as claimed in claim 4 in which said first and second teeth means comprise first and second sets of teeth configured and sized to substantially enclose the body of said parasite.

6. The forceps as claimed in claim 5 in which said first teeth means associated with said first arm are offset with respect to said second teeth means associated with said second arm along said first direction to avoid clamping or crushing any part of the parasite.

7. The forceps as claimed in claim 6 in which said first and second teeth means interdigitate when said arms are in said closed position.

8. The forceps as claimed in claim 7 in which said first and second interdigitating teeth means each increase monotonically in length from said distal end to said proximal end of each of said arms along said first direction.

9. The forceps as claimed in claim 8 in which each of said end portions at the distal end of each of said opposed arms has a flat end surface at the extreme distal end of said end portion, said surface being substantially perpendicular to said first direction.

10. The forceps as claimed in claim 9 in which one of said end portions has a surface acutely angled with respect to said end surface, and said acutely angled surface extends generally from said distal end towards said proximal end, and the other of said opposed end portions has a surface that mates with said acutely angled surface when said arms are in said closed position.

11. The forceps as claimed in claim 10 in which said opposed arms are approximately fourteen centimeters in length.

12. The forceps as claimed in claim 11 in which said first and second interdigitating teeth means each comprise five sets of teeth that vary in length from approximately four millimeters to approximately ten to twelve millimeters.

13. The forceps as claimed in claim 12 in which said opening is substantially oval, said oval having a major axis extending along the longest straight line connecting two points on the periphery of said oval, and a minor axis orthogonal to and smaller than said major axis.

14. The forceps as claimed in claim 13 in which said oval opening is formed so that the major axis of said oval is substantially perpendicular to said first direction and the major axis of said oval is also substantially parallel to said first and second teeth means.

15. The forceps as claimed in claim 14 in which said major axis is in the range of 0.8 to 1.2 millimeters.

16. The forceps as claimed in claim 10 in which said opposed arms are approximately six centimeters in length.

17. The forceps as claimed in claim 16 in which said first and second interdigitating teeth means comprise two sets of teeth that vary in length from approximately one to two millimeters to approximately two to three millimeters.

18. The forceps as claimed in claim 17 in which said opening is substantially oval, said oval having a major axis extending along the longest straight line connecting two points on the periphery of said oval, and a minor axis orthogonal to and smaller than said major axis.

19. The forceps as claimed in claim 18 in which said oval opening is formed so that the major axis of said oval is substantially perpendicular to said first direction and the major axis of said oval is also substantially parallel to said first and second teeth means.

20. The forceps as claimed in claim 19 in which said major axis is in the range of 0.3 to 0.5 millimeters.

21. The forceps as claimed in claim 1 in which said forceps are made out of stainless steel or metal alloy.

22. The forceps as claimed in claim 1 in which said forceps are made out of plastic.

* * * * *